(12) United States Patent
Colling (10) Patent No.: US 10,643,757 B1
(45) Date of Patent: May 5, 2020

(54) MOUNTING APPARATUS FOR CUSTOMIZED SHIELDING FROM RADIATION

(71) Applicant: Timothy P. Colling, Farmington Hills, MI (US)

(72) Inventor: Timothy P. Colling, Farmington Hills, MI (US)

( * ) Notice: Subject to any disclaimer, the term of this patent is extended or adjusted under 35 U.S.C. 154(b) by 0 days.

(21) Appl. No.: 16/172,764

(22) Filed: Oct. 27, 2018

(51) Int. Cl.
*G21F 3/00* (2006.01)
*A61B 6/10* (2006.01)
*A61G 13/10* (2006.01)

(52) U.S. Cl.
CPC ............... *G21F 3/00* (2013.01); *A61B 6/107* (2013.01); *A61G 13/10* (2013.01)

(58) Field of Classification Search
None
See application file for complete search history.

(56) References Cited

U.S. PATENT DOCUMENTS

| | | | | |
|---|---|---|---|---|
| 1,389,997 A * | 9/1921 | Sedgwick | ............... | F28F 9/10 122/511 |
| 3,984,696 A * | 10/1976 | Collica | ............... | A61B 6/107 250/519.1 |
| 5,006,718 A * | 4/1991 | Lenhart | ............... | A61B 6/107 250/515.1 |
| 5,152,486 A * | 10/1992 | Kabanek | ............... | A61G 13/10 108/49 |
| 5,678,267 A * | 10/1997 | Kinder | ............... | A61G 7/0507 5/428 |
| 8,378,326 B2 * | 2/2013 | Hunt | ............... | A61B 6/107 250/515.1 |
| 9,820,702 B2 * | 11/2017 | Osherov | ............... | A61B 6/548 |
| 9,867,583 B1 * | 1/2018 | Colling | ............... | A61B 6/107 |
| 9,877,688 B1 * | 1/2018 | Colling | ............... | A61B 6/107 |
| 10,004,466 B1 * | 6/2018 | Colling | ............... | A61B 6/107 |
| 2015/0308188 A1 * | 10/2015 | Lin | ............... | B60J 1/2033 242/375.3 |
| 2016/0199973 A1 * | 7/2016 | Wood | ............... | B25G 1/04 |
| 2017/0309356 A1 * | 10/2017 | Inanami | ............... | A61B 90/00 |
| 2018/0220977 A1 * | 8/2018 | Colling | ............... | G21F 3/00 |
| 2018/0226163 A1 * | 8/2018 | Colling | ............... | G21F 3/00 |

FOREIGN PATENT DOCUMENTS

KR         200458319 Y1 *   1/2018   ............... A47H 1/02

* cited by examiner

*Primary Examiner* — Michael J Logie
(74) *Attorney, Agent, or Firm* — Marin Patents IP; Gustavo Marin (57) ABSTRACT

A mounting apparatus for a shielding system for customized shielding of a patient or an operator from radiation. The shielding system is mounted on a rail of a table used for interventional medical procedures comprising a longitudinal rail edge. In use, the mounting apparatus is slidably engaged to a rail by mating a t-shaped groove to the rail. Extending from the mounting apparatus is one or more movable rods from which protective radio-opaque curtains are suspended.

9 Claims, 7 Drawing Sheets

MOUNTING APPARATUS FOR CUSTOMIZED SHIELDING FROM RADIATION

CROSS-REFERENCE TO RELATED APPLICATIONS

None.

BACKGROUND OF THE INVENTION

Field of the Art

The disclosure relates to the field of radiation shielding systems, and more particularly, a mounting apparatus for customizable radiation shielding system.

Discussion of the State of the Art

Radiation such as X-rays or computed tomography (CT) scans are performed frequently in hospitals for health examination or treatment purposes. Medical radiation involves applying radiation such as X-rays, gamma-rays, beta rays, injecting radioactive isotopes into the body, or administering them orally to take imaging studies or treat various diseases.

When the human body is exposed to radiation, cells can die, become malignant, or even mutate. If cells die, it can be harmful to tissues or organs. If DNA inside a cell is damaged, the cell can turn to cancer. If DNA damage occurs in a sperm or egg, it can lead to genetic problems such as congenital anomalies in the offspring.

Though in most hospitals, patients are given an explanation of the harms of radiation exposure and in some cases how much radiation they would be exposed to, little attention is paid to the effect of radiation on healthcare professionals. With an aging population and an increasing demand in radiation treatments, healthcare professionals are exposed to increased doses of radiation. Accordingly, healthcare professionals must wear manufactured protective clothing made of metal composites which are dense, warm and impervious, which causes discomfort and even physical pain among healthcare personnel. This reduces their performance and negatively affects the length of time they can work.

What is needed is a shielding system for customized protection from radiation in a medical environment that reduces the need for heavy, and uncomfortable protective clothing.

SUMMARY OF THE INVENTION

Accordingly, the inventor has conceived and reduced to practice, in a preferred embodiment of the invention, a mounting apparatus for customized shielding from radiation for a table used for interventional medical procedures. The mounting apparatus comprises a first side surface and an opposing second side surface, a front surface and an opposing back surface whereby the back surface comprises a longitudinally-extending t-shaped groove from the first side to the second side. The t-shaped groove is configured to be slidably engaged to a rail of an interventional medical procedure table so that upon engagement, the mounting apparatus has little or no movement in relation to the rail of the interventional medical procedure table. The apparatus further comprises a top surface and an opposing bottom surface, the top surface comprising one or more rod-receiving apertures (for example, a curtain rod, utility rod, or the like) that extends into the apparatus at least partially from the top surface, the one or more rod-receiving apertures have an entrance region and a plurality of slots extending radially from the one or more apertures, the plurality of slots being configured to be in registration with one or more cross-sections associated to a rod (for example, a curtain rod). The cross-section may be plurality of lugs extending radially from the proximal section of the rod to preclude a twisting motion of the rod when registered to the plurality of slots. The cross-section when registered to the slots keep the rod in-place where there is little or no movement of the rod in relation to the top surface.

The rods have a proximal section and a distal section that extends from the proximal section so that one or more radio-opaque curtains may be suspended from the distal section. In some embodiments, the rod may have a proximal, distal, and at least one intermediate adjacent sections, each of the intermediate adjacent sections being at an angle with respect to the adjoined adjacent section. In this regard, the radio-opaque curtains may be placed in any arrangement including underneath the table.

In some embodiments, the mounting apparatus may further comprise a threaded through-hole extending from the front surface to the back surface, whereby an anchoring can be introduced into the through hole and tightened for securely locking the mounting apparatus to the rail. In this regard, the anchoring post may comprise a threaded bolt having a lower end portion that is received by the threaded through-hole and an upper end portion that terminates in an end member that can be gripped by the hand of a healthcare professional.

In some embodiments, the distal section of the rod may extend horizontally across the interventional medical procedure table or in parallel with a longitudinal edge of the rail. In another embodiment, the rod orientation may be in a generally horizontal orientation. In another embodiment, the rod orientation may be in a forward orientation.

Once the rod is inserted into the aperture, the rod can be twisted within the aperture to register the cross-section to a different set of slots of the plurality of slots thereby changing the angle of the rod and any radio-opaque curtains.

In some embodiments, a single mounting apparatus may comprise two or more apertures on the top surface whereby multiple rods may be engaged. It should be noted that in this configuration, each rod may be in a same or different orientation. In some embodiments, more than one mounting apparatus may be place adjacent to each other to achieve a similar effect. In some embodiments the plurality of mounting devices may be daisy chained and attached to each other using a fastener or adhesive.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary and are not to be considered as limiting of the scope of the invention or the claims herein in any way.

DETAILED DESCRIPTION

The inventor has conceived, and reduced to practice, in a preferred embodiment of the invention, a mounting apparatus for customized shielding from radiation for a table used for interventional medical procedures.

One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Detailed embodiments of the present invention are disclosed herein; however, it is to be understood that the disclosed embodiments are merely exemplary of the invention that may be embodied in various and alternative forms. The figures may not necessarily be to scale; some features may be exaggerated or minimized to show details of particular components. Therefore, specific structural and functional details disclosed herein are not to be interpreted as limiting, but merely as a representative basis for teaching one skilled in the art to variously employ the present invention.

Headings of sections provided in this patent application and the title of this patent application are for convenience only and are not to be taken as limiting the disclosure in any way.

Figure 1A:
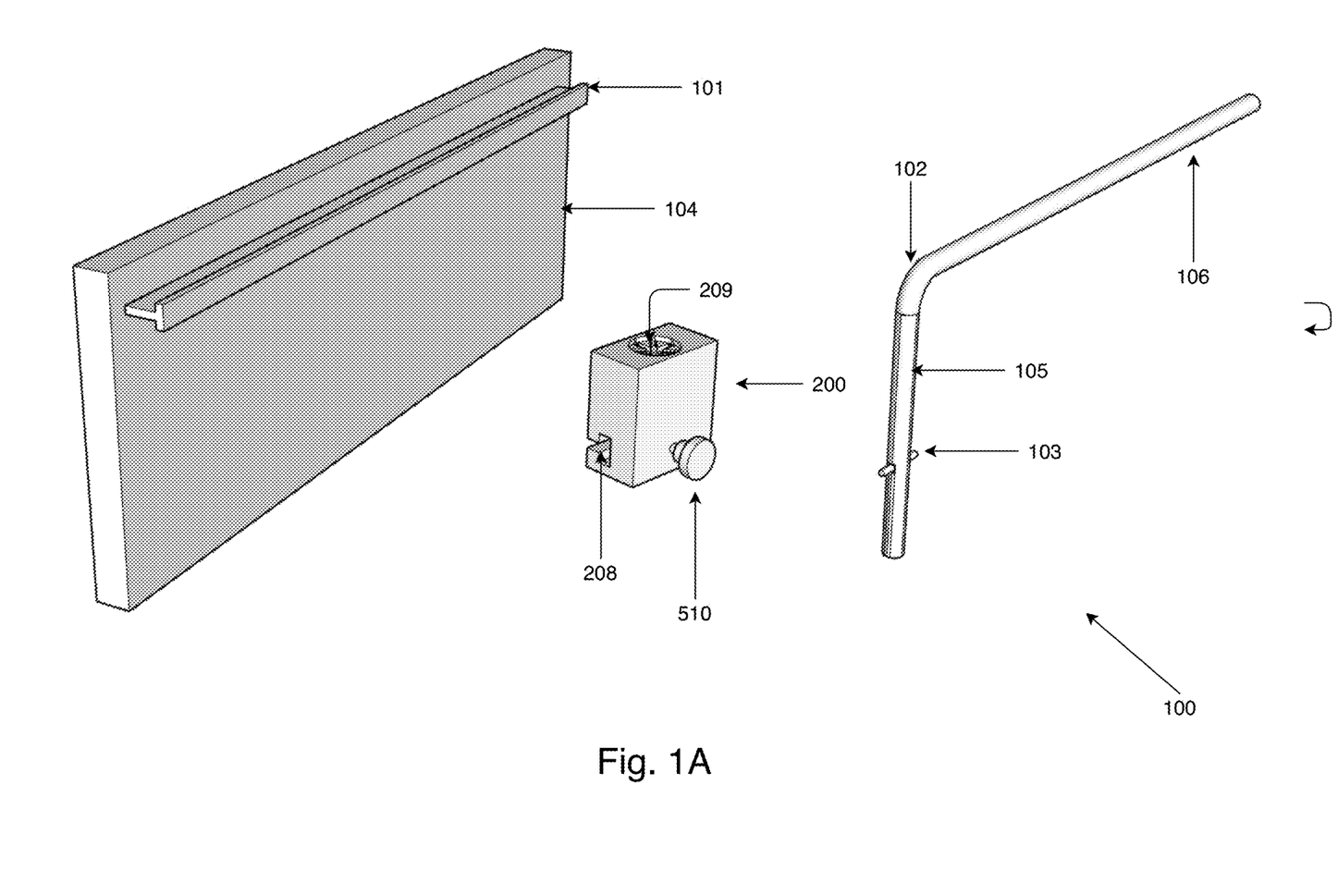
FIG. 1A is a perspective view of typical elements for a customized shielding system, according to a preferred embodiment of the invention.

FIG. 1A is a perspective view of typical elements for a customized shielding system, according to a preferred embodiment of the invention. According to the embodiment, disclosed is a shielding system 100 for use in customized shielding from radiation. The mounting apparatus 200 comprising t-shaped groove 208 that may be slidably mountable on longitudinal t-shaped rail 101 of intervention medical procedure table 104. Mounting apparatus 200 may comprise, at least one or more rod-receiving apertures 209 extend from top surface 205 to opposing bottom surface 206 (referring to FIGS. 2A and 2B). Table 104 may have a surface that, for example, supports a patient.

Shielding system 100 may further comprise rod 102 comprising proximal section 105 and extending from proximal section 105, a distal section 106. In in some embodiments, at least one intermediate sections (not shown). Proximal section 105 may comprise at least one cross-section 103.

It should be appreciated by one with ordinary skill in the art that rod 102 may be any shape or have different and/or intermediate sections or segments whereby one or more radio-opaque curtains 601A . . . N (referring to FIG. 6) may be hung from distal section 106 to provide shielding from radiation and to allow flexibility in adapting to operator and patient examination requirements. It will be appreciated that the curtains 601A . . . N are preferably formed from a radiation absorbent material.

In some embodiments, rod 102 may be in a generally horizontal orientation (for example, in parallel to rail 101 as shown). In another embodiment, rod 102 may be in a forward orientation. In some embodiments, rod 102 may comprise a proximal, distal, and at least one intermediate adjacent sections, whereby each of the intermediate adjacent sections may be at an angle between 0 and 180 degrees with respect to the adjacent section such that the curtain arrangement may shield radiation, for example, below or above table 104.

In some embodiments, mounting apparatus 200 may comprise locking means 510 (referring to FIG. 5) to secure or lock mounting apparatus 200 to prevent movement.

Figure 1B:
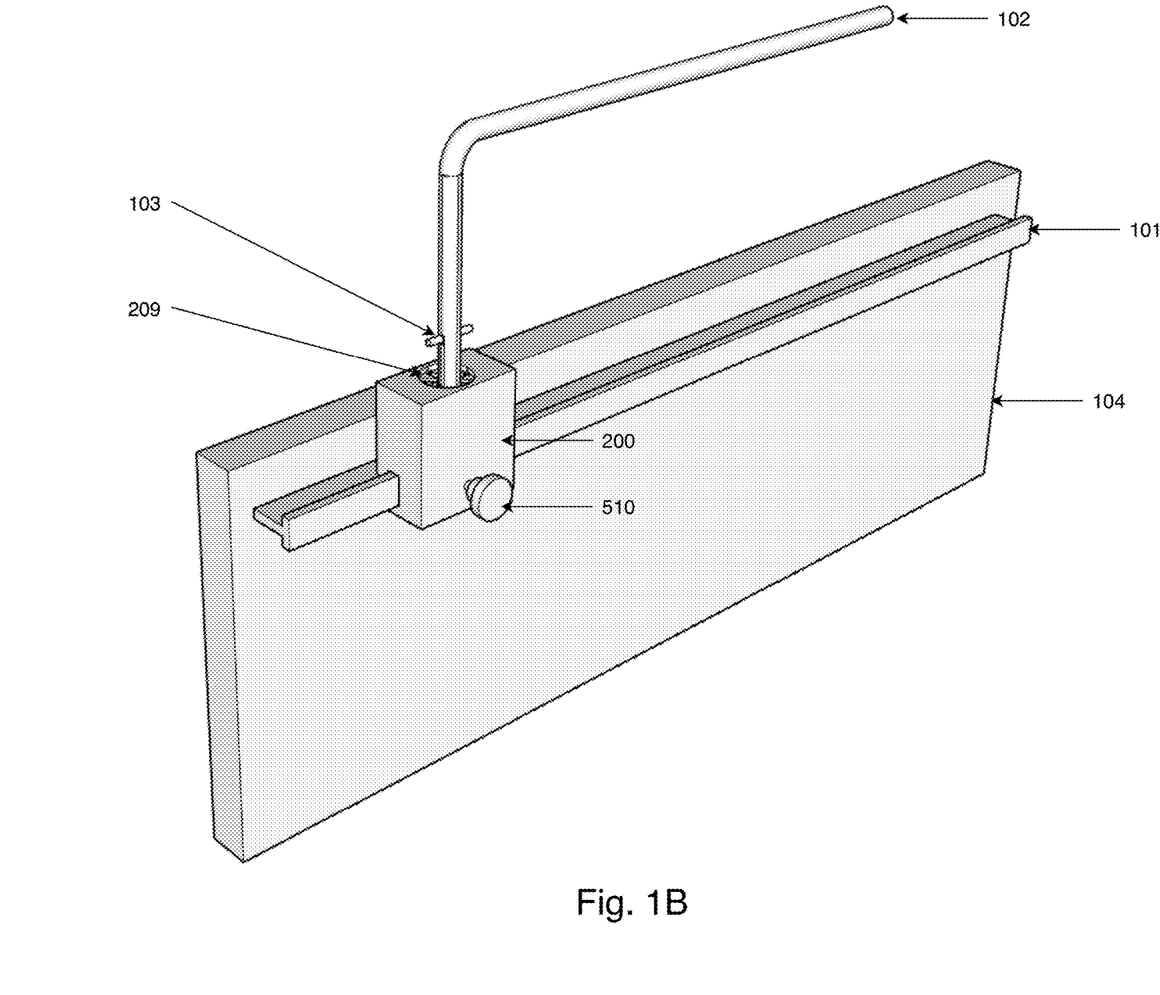
FIG. 1B is a perspective view of a partially mated rod and aperture for customized shielding of radiation, according to a preferred embodiment of the invention.

FIG. 1B is a perspective view of a partially mated rod and aperture for customized shielding of radiation, according to a preferred embodiment of the invention. According to the embodiment, mounting apparatus 200 is slidably mated to rail 101 such that once engaged there is little or no movement of mounting device 200 in relation to rail 101. In some embodiments locking means 510 to constrain movement of mounting apparatus 200 in relation to rail 101. Further according to the embodiment, an entrance region of rod-receiving aperture 209 is engaged by the proximal end of rod 209.

Figure 1C:
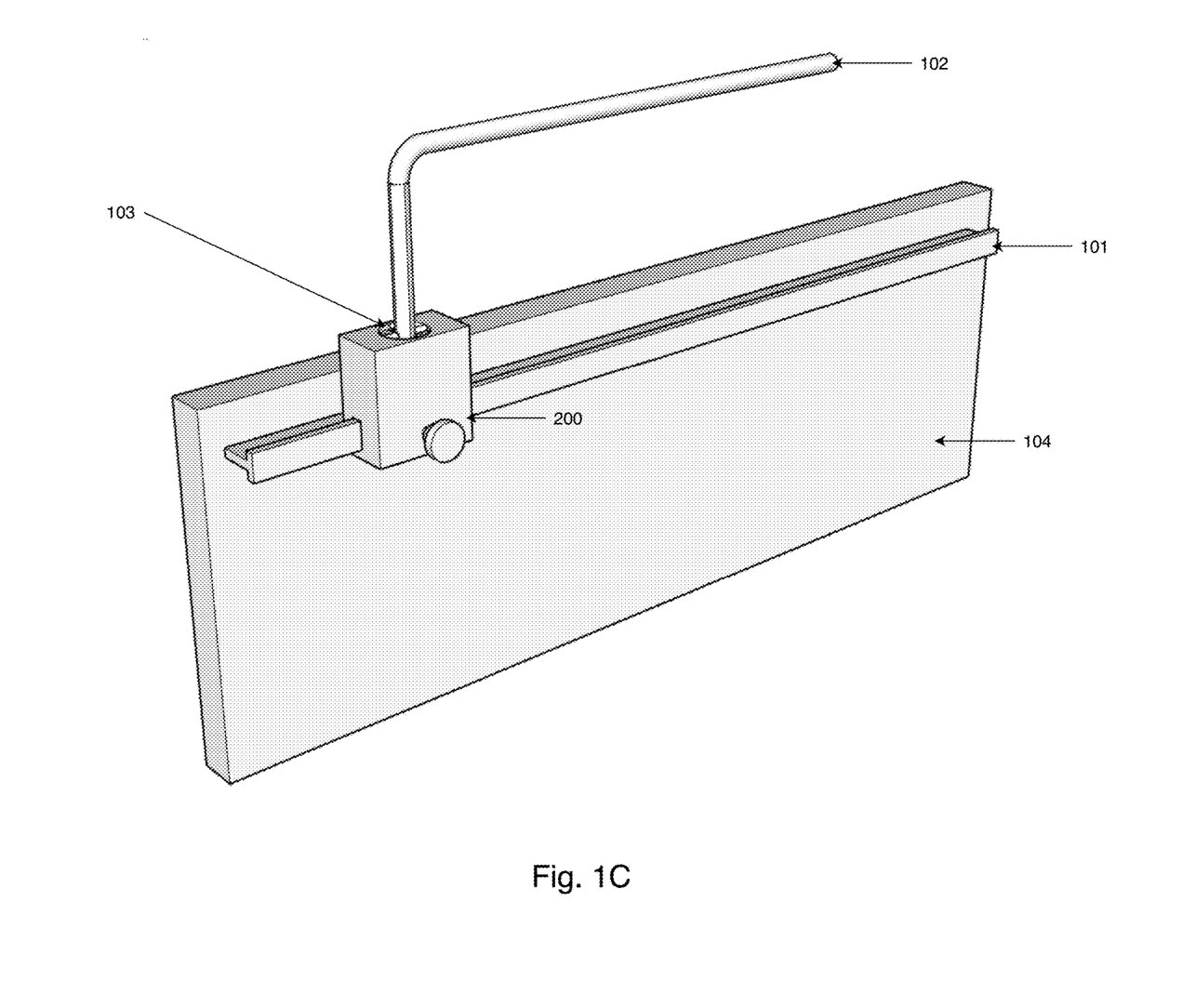
FIG. 1C is a perspective view of a mated rod and aperture for customized shielding of radiation, according to a preferred embodiment of the invention.

FIG. 1C is a perspective view of a mated rod and aperture for customized shielding of radiation, according to a preferred embodiment of the invention. According to the embodiment, rod-receiving aperture 209 of mounting apparatus 200 is mated by the proximal end of rod 102 such that cross-section 103 is registered to at least a portion of radially extending slots 303A . . . N (referring to FIG. 3). Upon registration of cross-section 103, there is little or no movement of the rod in relation to the mounting apparatus 200. In some embodiments, rod 102 may comprise more than one cross-sections 103. Rod 102 may be twisted within the aperture to register the cross-section 103 to a different set of slots of the plurality of slots 303A . . . N to, for example, change the arrangement of the distal section of rod 102.

Figure 2A:
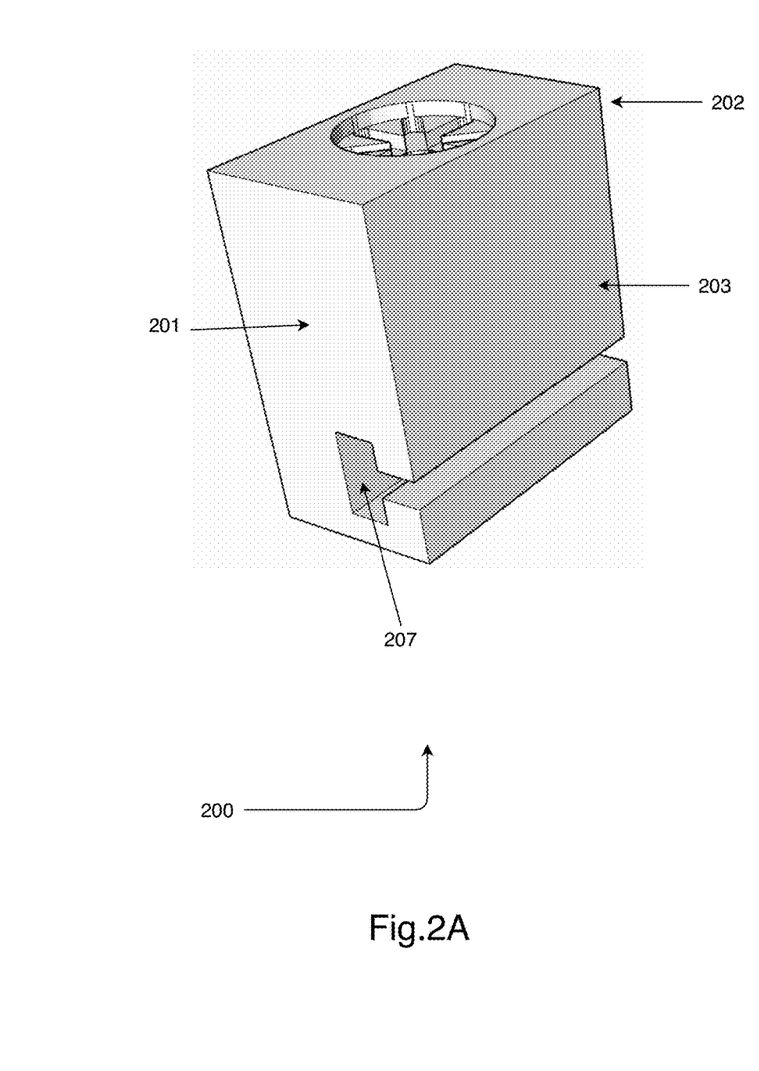
FIG. 2A is a left elevational view of a mounting apparatus, according to a preferred embodiment of the invention.
Figure 2B:
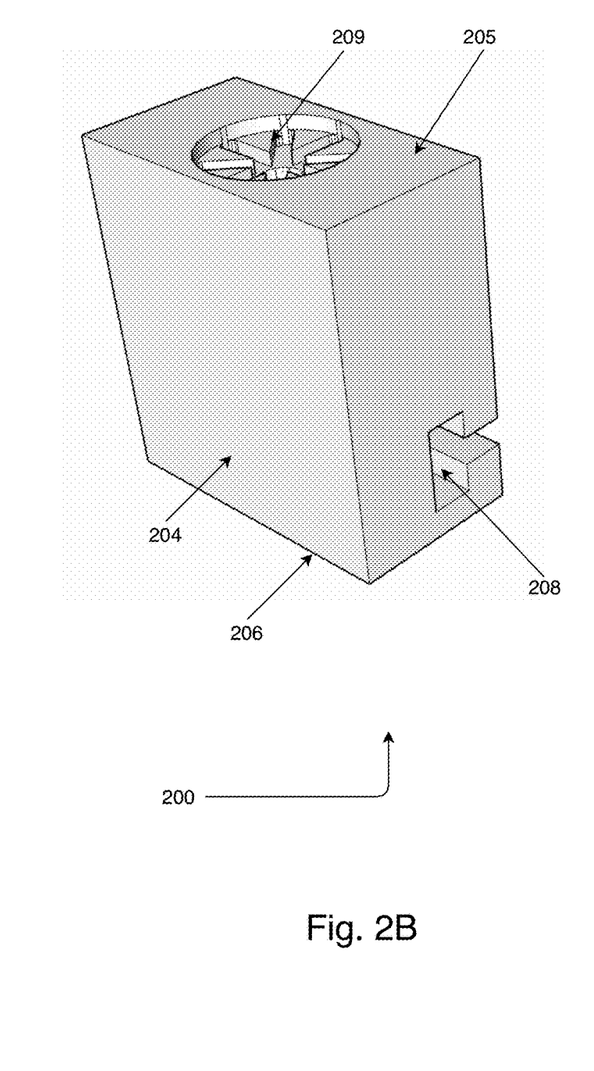
FIG. 2B is a right elevational view of a mounting apparatus, according to a preferred embodiment of the invention.

FIGS. 2A and 2B are elevational views of a mounting apparatus, according to a preferred embodiment of the invention. According to the embodiment, mounting apparatus 200 comprises first side surface 201 and an opposing second side surface 202, a front surface 204 and an opposing back surface 203, the back surface comprising a longitudinally-extending t-shaped groove 208 with a t-groove surface 207. The t-shapes groove extends from first side surface 201 to second side surface 202, the t-shaped groove is configured to be slidably engaged to a rail 101 of an interventional medical procedure table (referring to FIGS. 1B and 1C) so that upon registration, there is little or no movement of mounting device 200 in relation to rail 101.

Further according to the embodiment, mounting apparatus 200 further comprises top surface 205 and opposing bottom surface 206. Top surface 205 comprises one or more rod-receiving apertures 209 that extend at least partially from top surface 205 into a body portion of mounting apparatus 200. In some embodiments, aperture 209 is a through hole extending to bottom surface 206. Rod-receiving aperture 209 is configured to be mated with rod 102 as shown in FIGS. 1B and 1C having at least one cross section to sit within a plurality of slots 303A . . . N.

Although mounting apparatus 200 is depicted as generally cubical, it will be appreciated that mounting apparatus 200 may be shaped in various geometries and sizes and may have nonparallel faces that, in some embodiment, may or may not be planar.

Figure 3:
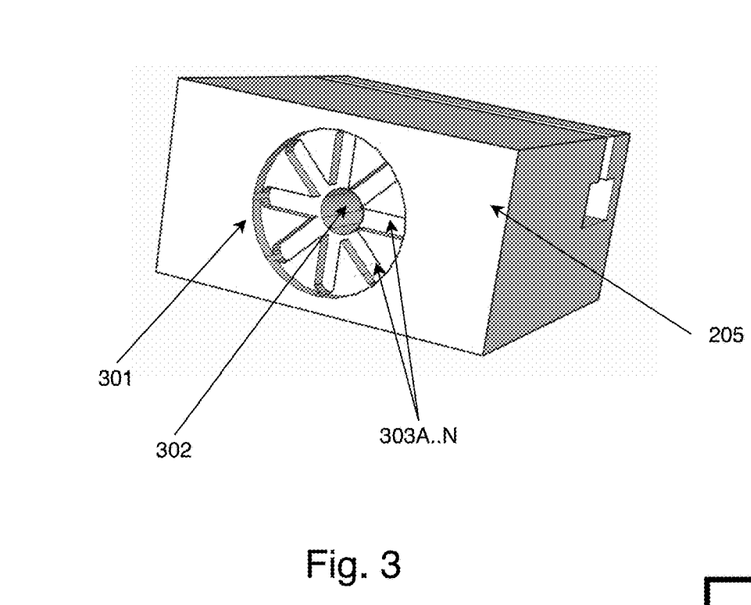
FIG. 3 is a top view of a mounting apparatus depicting a rod-receiving aperture, according to a preferred embodiment of the invention.

FIG. 3 is a top view of a mounting apparatus depicting a rod-receiving aperture, according to a preferred embodiment of the invention. According to the embodiment, top surface 205 of mounting apparatus 200 comprises a rod-receiving aperture section 301 (that is, an exploded view of rod-receiving aperture 209). According to the embodiment, rod-receiving aperture section 301 comprises an entrance region 302 and a plurality of slots 303A . . . N extending radially from the entrance region 302, the plurality of slots 303A . . . N being configured to be in registration with one or more cross-sections 103 of rod 102. In a preferred embodiment, rod-receiving aperture 209 may comprise four or eight slots 303A . . . N; however, it should be appreciated that any number of slots may be configured. Slots 303A . . . N may be configured to engage a cross section 103 (for example, one or more lugs) that extends radially from the proximal section of rod 102 such that the cross-section 103 sits within the slots to preclude a twisting motion of rod 102 when seated within an associated aperture. This feature influences rod 102 positioning regardless of orientation. It should be appreciated that rod 102 may be twisted (for example, with a slight lifting and turning motion by a user) such that while rod 102 while least partially engaged to entrance region 302, a different set of slots may be engaged by cross section 103 such that the orientation of rod 102 is changed. It should be appreciated that in a preferred embodiment, slots 303A . . . N may be rounded to accept a rounded cross section 103; however, in other embodiments, slots 303A . . . N may be other shapes such as square, rectangular, triangular, or the like to mate with a similarly shaped cross section 103.

Figure 4:
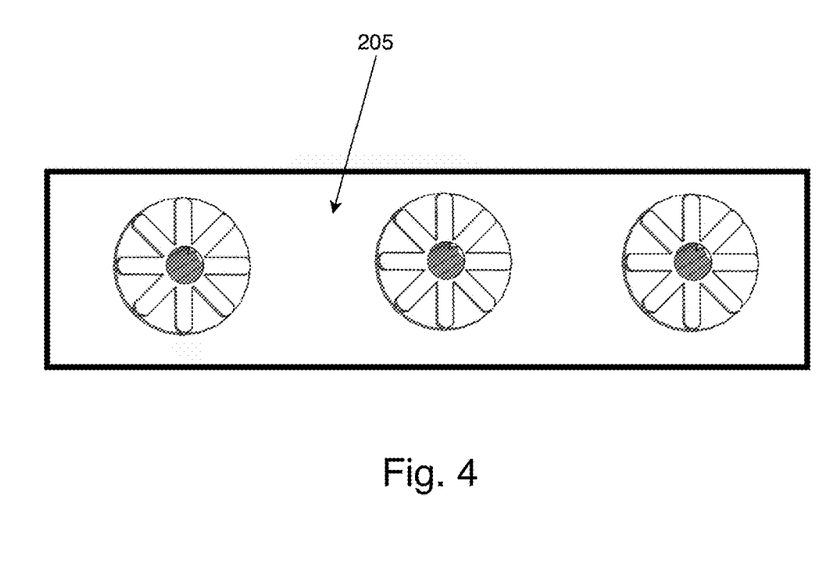
FIG. 4 is an exemplary top view depicting a plurality of rod-receiving apertures of a mounting apparatus, according to an embodiment of the invention.

FIG. 4 is an exemplary top view depicting a plurality of rod-receiving apertures of a mounting apparatus, according to an embodiment of the invention. According to the embodiment, a plurality of rod-receiving aperture section 301 (referring to FIG. 3) may be configured on one mounting apparatus 200 such that more than one rods 102 may be supported by a single mounting apparatus 200. In this regard, the more than one rods 102 may be configured to be in the same, similar or different orientation in relation to the other rods 102.

Figure 5:
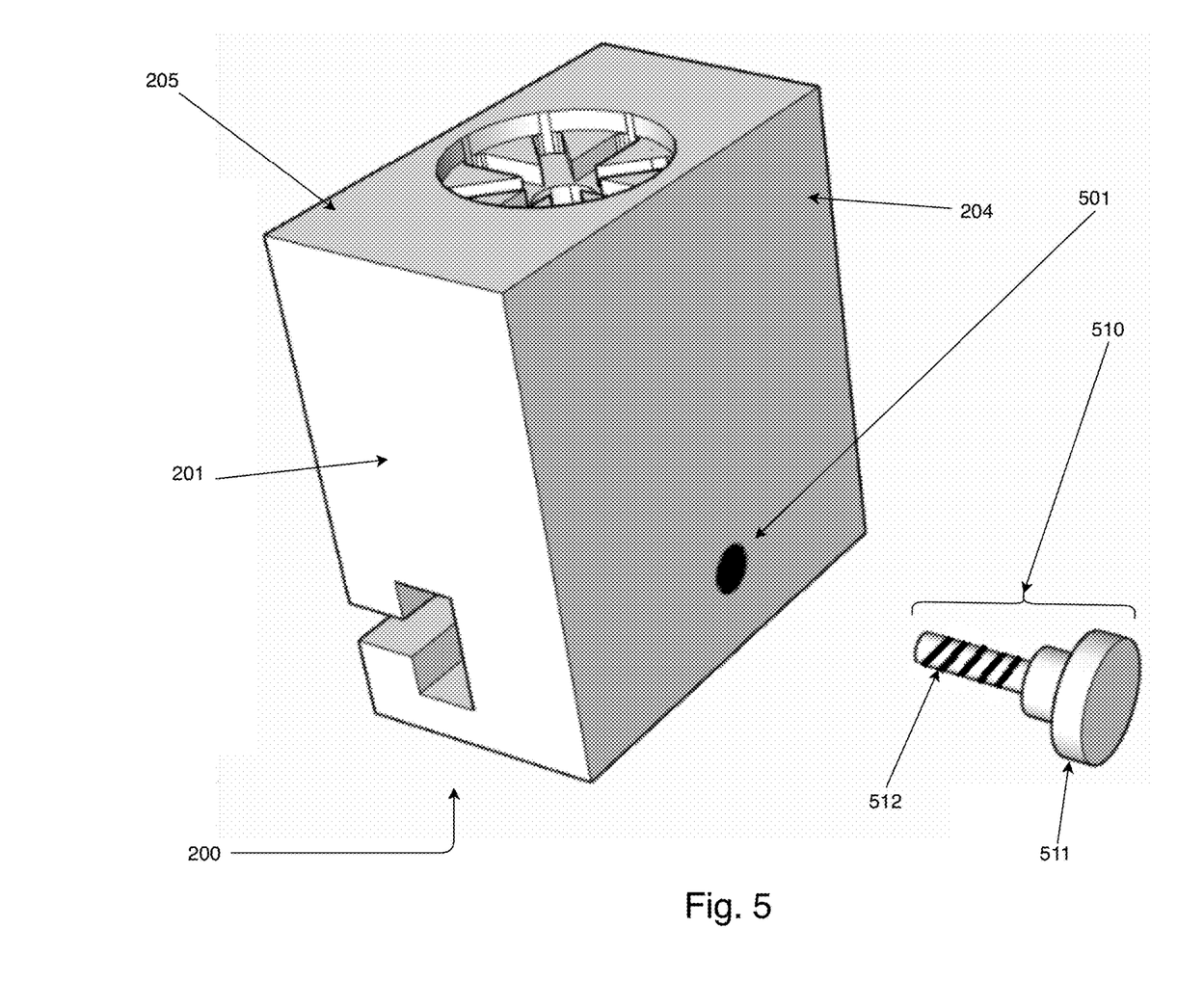
FIG. 5 is a side view depicting an optional locking mechanism of a mounting apparatus, according to an embodiment of the invention.

FIG. 5 is a side view depicting an optional locking mechanism of a mounting apparatus, according to an embodiment of the invention. According to the embodiment, to secure a mounting apparatus 200 in relation to rail 101 of table 104 used for interventional medical procedures, a means for securing or locking is provided. Such locking means 510 comprises, for example, a threaded bolt having a lower end portion 512 and head portion 511, whereby lower end portion 512 may be received by a threaded through-hole 501 that extends from front surface 204 surface to the t-groove surface 207. Head portion 511 (such as a knurled knob) may be gripped by a hand. In some embodiments, lower end portion 512 may be tapered and through hole 501 may not be threaded to use friction to secure the end portion 512 within the through hole 501.

Figure 6:
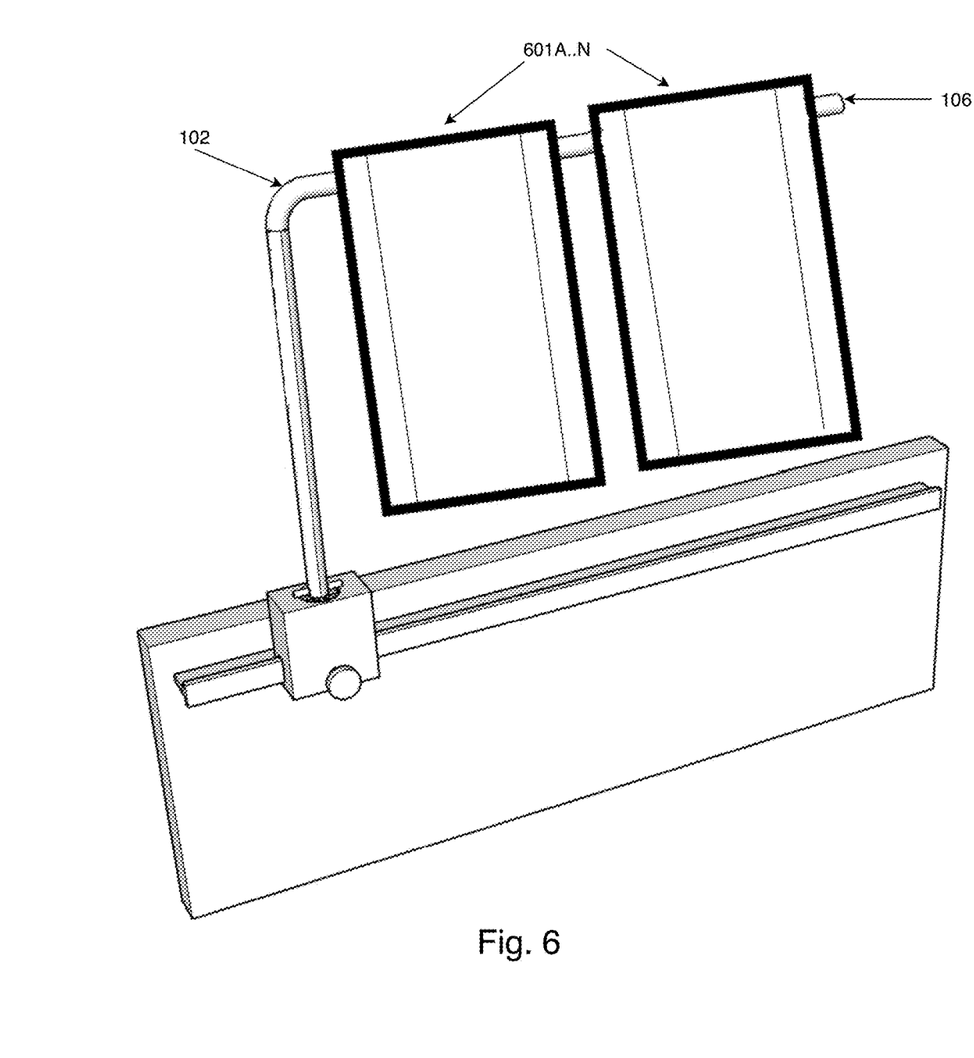
FIG. 6 is a curtain arrangement using a mounting apparatus, according to an embodiment of the invention.

FIG. 6 is a curtain arrangement using a mounting apparatus, according to an embodiment of the invention. According to the embodiment, one or more radio-opaque curtains 601A . . . N can be hung from the distal section 106 of rod 102 to allow flexibility in adapting to operator and patient examination requirements. It will be appreciated that the curtains 601A . . . N are preferably formed from a radiation absorbing material (for example, block radiation, electromagnetic energy, etc.). Such curtains 601A . . . N may for example be 50 cm long by 66 cm wide; but curtains 601A . . . N may be of any length and width. Further, the curtains may have any desired radiation attenuation characteristics.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

The skilled person will be aware of a range of possible modifications of the various embodiments described above. Accordingly, the present invention is defined by the claims and their equivalents.

What is claimed is:

1. A mounting apparatus for customized shielding from radiation for a table used for interventional medical procedures comprising:
   a first side surface and an opposing second side surface;
   a front surface and an opposing back surface, the back surface comprising a longitudinally-extending t-shaped groove from the first side to the second side, the t-shaped groove configured to be slidably engaged to a rail of an interventional medical procedure table so that upon registration, there is little or no movement of the mounting apparatus in relation to the rail;
   a top surface and an opposing bottom surface, the top surface comprising one or more rod-receiving apertures that extends at least partially from the top surface, the one or more rod-receiving aperture having an entrance region and a plurality of slots, the plurality slots extending radially from the one or more apertures, the plurality of slots being configured to be in registration with one or more cross-sections associated to one or more rods; wherein upon registration of the one or more cross-sections, there is little or no movement of the rod in relation to the top surface;

wherein the one or more rods comprise a proximal section and a distal section that extends from the proximal section so that one or more radio-opaque curtains can be suspended from the distal section;

wherein the one or more cross-sections is a plurality of lugs extending radially from the proximal section of the rod to preclude a twisting motion of the rod when registered to the plurality of slots.

2. The mounting apparatus of claim 1, further comprising a threaded through-hole extending from the front surface to the back surface, the through hole operable to receive an anchoring post for locking the mounting apparatus to the rail.

3. The mounting apparatus of claim 2, wherein the anchoring post comprises a threaded bolt having a lower end portion that is received by the threaded through-hole and an upper end portion that terminates in a head portion that is operable to be gripped by a hand.

4. The mounting apparatus of claim 1, wherein the distal section of the rail extends horizontally across the interventional medical procedure.

5. The mounting apparatus of claim 1, wherein one rod orientation is a generally horizontal orientation relative to the interventional medical procedure table.

6. The mounting apparatus of claim 1, wherein the one or more rods are operable to be twisted within the aperture to register the one or more cross-sections to a different set of slots of the plurality of slots.

7. The mounting apparatus of claim 1, wherein the top surface comprises two or more apertures, the two or more apertures each having a rod engaged, each rod in a same or different orientation.

8. The mounting apparatus of claim 1, wherein the one or more rods further comprises at least one intermediate sections, each of the intermediate sections being at an angle between 0 and 180 degrees with respect to another adjoined intermediate section.

9. The mounting apparatus of claim 8, wherein the one or more intermediate sections are arranged so that the one or more radio-opaque curtains are suspended below the table.

* * * * *